United States Patent [19]

McLeod et al.

[11] Patent Number: 4,969,895

[45] Date of Patent: Nov. 13, 1990

[54] APPARATUS AND METHOD FOR DETERMINING THE TENSION ON A LIGAMENT GRAFT

[75] Inventors: William McLeod; Paul Wisnewski; David Evans; Mark Gosney, all of Memphis, Tenn.

[73] Assignee: Richards Medical Company, Memphis, Tenn.

[21] Appl. No.: 300,994

[22] Filed: Jan. 23, 1989

[51] Int. Cl.[5] .............................................. A61F 5/04
[52] U.S. Cl. ..................................... 606/96; 606/102; 606/103; 606/104
[58] Field of Search .................... 128/774, 782, 92 V, 128/92 VP, 92 VT, 92 VL, 92 VR, 92 R, 305.1; 623/13, 66; 606/87, 96, 102, 103, 104

[56] References Cited

U.S. PATENT DOCUMENTS

| | | |
|---|---|---|
| 3,896,500 | 7/1975 | Rambert et al. |
| 3,953,896 | 5/1976 | Treace |
| 3,973,277 | 8/1976 | Semple et al. |
| 4,050,464 | 9/1977 | Hall |
| 4,246,660 | 1/1981 | Wevers |
| 4,364,389 | 12/1982 | Keller |
| 4,501,266 | 2/1985 | McDaniel |
| 4,538,768 | 8/1985 | Hourahane et al. ............. 128/305.1 |
| 4,583,555 | 4/1986 | Malcom et al. |
| 4,712,542 | 12/1987 | Daniel et al. |
| 4,739,751 | 4/1988 | Sapega et al. ................. 128/92 VL |
| 4,768,139 | 11/1987 | Dunbar, IV ................... 128/305.1 |
| 4,823,780 | 4/1989 | Odensten et al. ................. 623/13 |

OTHER PUBLICATIONS

Penner, Darrell A., MD. et al. "An In Vitro Study of Anterior Cruciate Ligament Graft Placement and Isometry," The American Journal of Sports Medicine, vol. 16, No. 3, pp. 238-243.

Primary Examiner—Randall L. Green
Assistant Examiner—K. M. Reichle
Attorney, Agent, or Firm—Kirkpatrick & Lockhart

[57] ABSTRACT

An instrument for determining the variation in tension of a ligament graft extending between first and second proposed fixation sites positioned on first and second articulated bones, respectively, comprises a yoke which carries a device for securing the yoke to one of the first and second bones. A yoke plate is rotatably carried by the yoke. A main housing is adapted for connection to the yoke plate. A sled is slidably carried by the main housing. The sled is adapted for connection to the ligament graft. A mechanism is provided for adjusting the position of the sled relative to the housing so as to place a desired degree of tension on the ligament graft. A transducer is associated with the mechanism for adjusting for determining changes in tension, if any, from the desired degree of tension as the first and second bones are moved relative to one another.

15 Claims, 5 Drawing Sheets

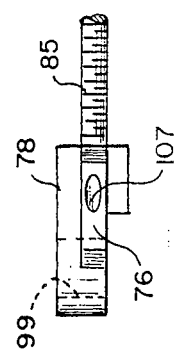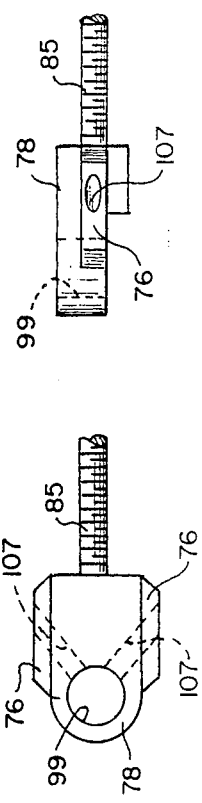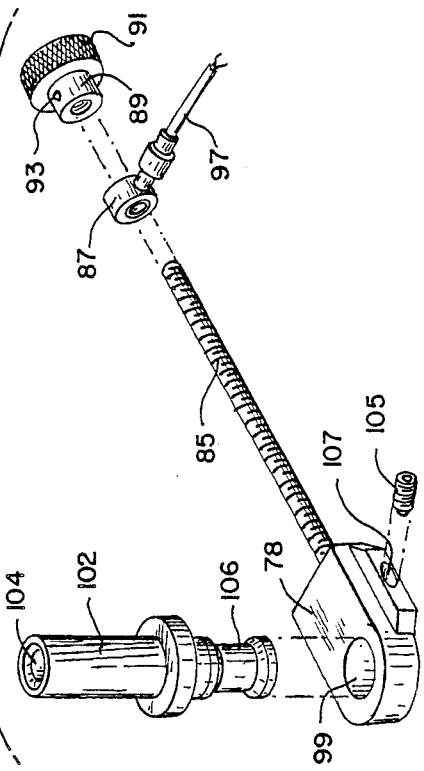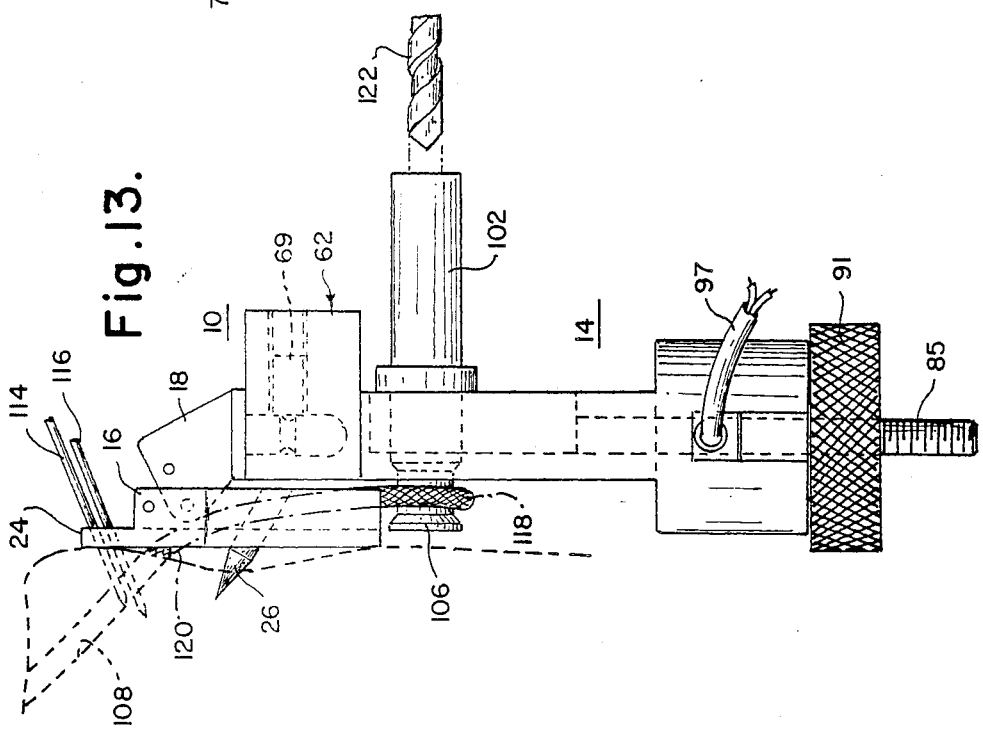

APPARATUS AND METHOD FOR DETERMINING THE TENSION ON A LIGAMENT GRAFT

BACKGROUND OF THE INVENTION

1. Field of the Invention

The present invention is directed generally to determining the tension on a replacement device and more particularly to the tension on, and hence the optimal placement of, a cruciate ligament replacement.

2. Description of the Prior Art

It is known to replace various parts of the human body with artificial parts. In one application, ligaments which have been damaged beyond repair or diseased can be replaced with artificial ligaments. The artificial ligament should function the same as, or as closely as possible to, the original ligament. To achieve proper functioning of the artificial ligament, the position of the ligament must be precisely determined so that the tension experienced by the ligament as the articulated bones to which it is attached move relative to each other approximates that experienced by the original ligament. However, due to the unavoidable differences in joint configurations (both geometric and kinematic) from one patient to the next in the normal knee, which is compounded in joints which have been previously operated upon, are diseased, or the like, the optimal placement of any device purporting to replicate the function of the original is not obvious without precise measurements of the nature of the forces to be experienced in situ.

U.S. Pat. No. 4,712,542 discloses a method and apparatus for establishing in situ ligament graft orientation and isometry, particularly for replacement of the anterior and posterior cruciate ligaments. The ligament graft is extended from one fixation site and is attached to a sled slidably carried by a frame. The frame is skeletally mounted to the other fixation site. A thumb nut and lead screw assembly carried by the frame are operative to compress a spring in the sled and move the sled in a direction effective to increase the tension in the graft. A pointer cooperates with force indicia to provide an indication of force while two means are provided for indicating the longitudinal position of the sled relative to the frame. Various measurements are taken with the articulated bones at various degrees of flexion and the ligament graft exposed to a constant tension. Isometry is achieved when the relative position of the frame and sled remain substantially unchanged through the entire range of motion.

The aforementioned device is somewhat cumbersome to use in that for each position of the articulated bones, the pointer must be read to insure that the force on the ligament graft is constant. If not, then the thumb nut must be operated to reestablish the desired tension. Thereafter, the position of the sled relative to the frame is determined. After several readings, if the position of the sled relative to the frame stays within acceptable limits, the fixation sites are deemed acceptable. Additionally, error may be introduced in the aforementioned device by virtue of the use of the spring in line with the ligament graft. The spring's expansion and contraction effectively changes the fixation site thus introducing errors in the tension measurements.

The need exists for an apparatus which is easy to use and provides an accurate reading of the tension experienced by the ligament with respect to proposed fixation sites. Preferably, a continuous reading of the tension is provided so that inferences needn't be drawn based on changes in length at a few points within the range of movement of the articulated bones.

SUMMARY OF THE PRESENT INVENTION

The present invention in its broadest form is directed to an instrument for determining the variation in tension of a ligament graft extending between first and second proposed fixation sites positioned on first and second articulated bones, respectively. The instrument comprises a yoke which carries a device for securing the yoke to one of the first and second bones. A yoke plate is rotatably carried by the yoke. A main housing is adapted for connection to the yoke plate. A sled is slidably carried by the main housing. The sled is adapted for connection to the ligament graft. A mechanism is provided for adjusting the position of the sled relative to the housing so as to place a desired degree of tension on the ligament graft. A transducer is associated with the mechanism for adjusting for determining changes in tension, if any, from the desired degree of tension as the first and second bones are moved relative to one another.

The present invention also includes a method of using the instrument of the present invention which method comprises the steps of positioning an impactor on a footplate; aligning an alignment pin of the impactor in a bore in one of the first and second bones; securing the footplate to one of the first and second bones; removing the impactor and connecting a housing carrying a sled, a mechanism for adjusting the position of the sled relative to the housing, and a transducer to the footplate; connecting the ligament graft to the sled; adjusting the tension on the ligament graft to place a desired degree of tension on the ligament graft; and measuring changes in tension from the desired degree of tension as the first and second bones are moved relative to one another.

The instrument and method of the present invention are particularly well suited for use in the replacement of the anterior and posterior cruciate ligaments of the knee.

The instrument of the present invention provides a transducer which is in line with the ligament graft. Because the transducer's linear dimension does not change, no error is introduced by virtue of changing the proposed fixation site. Additionally, a continuous reading is provided throughout the full range of motion of the articulated bones rather than a few data points at selected degrees of flexion. Finally, the instrument provides a direct reading of the in situ tension such that conversions or extrapolations are unnecessary. Those and other advantages and benefits of the present invention will become apparent from the Description of a Preferred Embodiment hereinbelow.

BRIEF DESCRIPTION OF THE DRAWINGS

In order that the present invention may be easily understood and readily practiced, a preferred embodiment will now be described, by way of example only, in conjunction with the following figures wherein:

FIGS. 9 and 9A illustrate top and side views, respectively, of a sled and tension bolt;

FIG. 10 is an exploded view of the parts carried by the sled and tension bolt;

FIG. 13 illustrates the tensiometer connected to the footplate while the footplate is firmly connected to the tibia and in the unlocked positioned for drilling of a screw guide hole in the tibia.

DESCRIPTION OF A PREFERRED EMBODIMENT

Introduction

Figure 1:
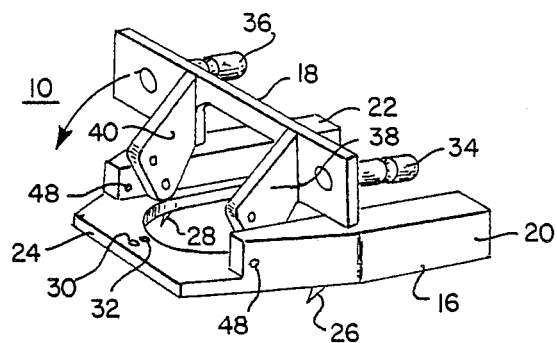
FIG. 1 is a perspective view of a footplate in an unlocked position.
Figure 4:
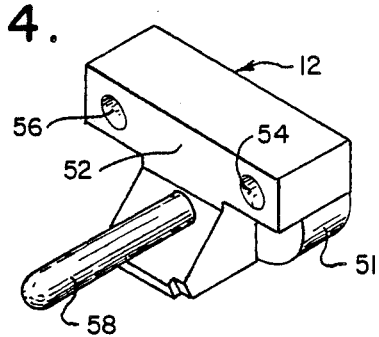
FIGS. 4 and 5 are front and rear perspective views, respectively, of an impactor.
Figure 5:
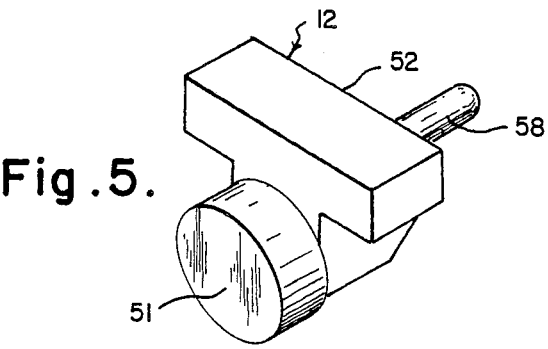
Figure 7:
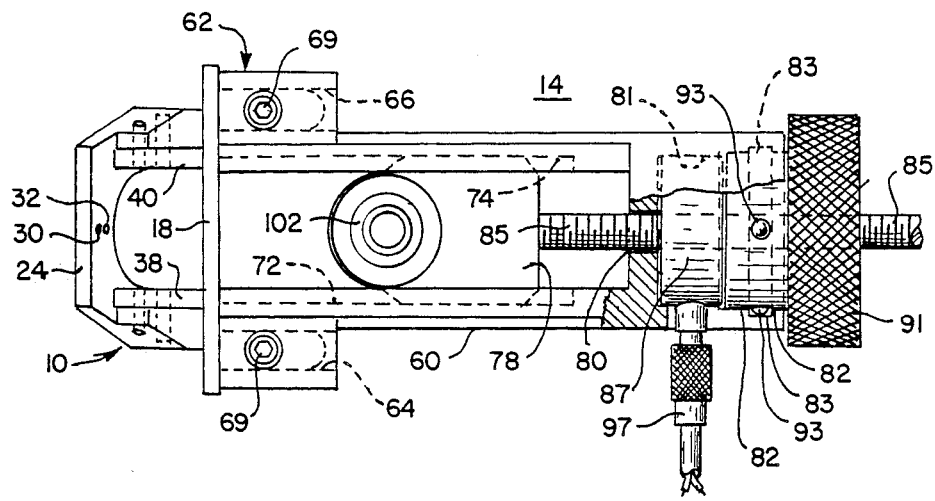
FIG. 7 is a top plan view, with parts broken away, of a full tensiometer assembly.

The instrument of the present invention is comprised of three parts, a footplate 10 illustrated in FIG. 1, an impactor/alignment device 12 illustrated in FIGS. 4 and 5, and a tensiometer assembly 14 illustrated in FIG. 7. The instrument is primarily intended for use in determining the optimal placement of a ligament graft, and is particularly well suited for determining the optimal placement of a cruciate ligament replacement. The replacement device may be used in conjunction with any of several options such as a tissue graft, prosthetic, etc. The use of the present invention is not dependent on the nature of the proposed replacement device.

It is important to understand that at the present time it is not possible to replace the exact kinematics of the knee. However, an acceptable set of kinematics can be provided but such acceptability can only be judged by precise measurements. The primary use of the instrument of the present invention is therefore to allow the measurement of the variation in tension that occurs in the replacement device as a result of the placement parameter selection.

Tension is first tested by placing a trial device from the femur, through the joint space, and out of the tibia. The trial device must be a small diameter device capable of sustaining a tension load and having an elastic spring constant similar to the ultimate replacement device. The trial device will be fixed at the femoral end to the femur and the tensiometer 14 is then interposed between the trial device and the tibia. Any regimen of tests can now be applied to the joint to determine the variation in tension that will occur in the final replacement device. Those forces can be measured without allowing any motion of the tibia relative to the femur that would not occur with the final device in place.

The load measuring device of the present invention is a solid state device or a load cell. An essential feature of the load cell is that it's spring constant or unit deformation per unit load is very small. Any load measuring device that satisfies that criteria is satisfactory. That is of critical importance because the measuring device is interposed in line with the replacement device and any deformation or elongation of the measurement device will distort the system and falsify the apparent load.

The trial device is small in diameter to allow the bony tunnels to be small enough that they can be replaced if necessary to obtain the best replacement kinematics for the joint. When an acceptable set of mechanics has been determined, the trial device is removed and the bony tunnels enlarged to accommodate the device being used to replace the ligament. The instrument of the present invention may then be used again to apply the proper tension to the final device.

Construction of the Present Invention

Figure 2:
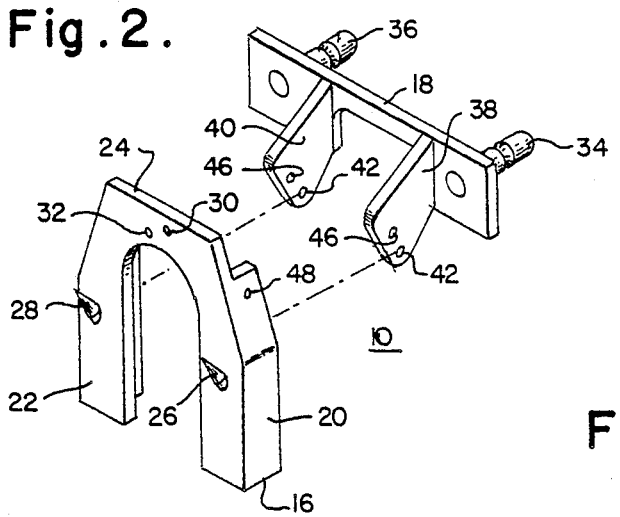
FIGS. 2 and 3 are exploded, perspective views taken from opposite sides of the footplate illustrated in FIG. 1.
Figure 3:
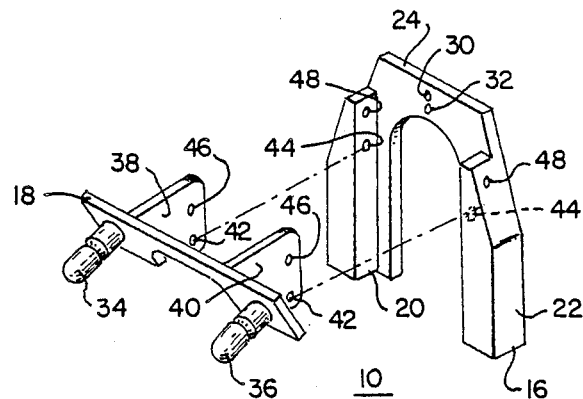

A perspective view of the footplate 10 is illustrated in FIG. 1 while two different exploded, perspective views are illustrated in FIGS. 2 and 3. The footplate 10 is constructed of a yoke 16 and a yoke plate 18. The yoke 16 is a substantially U-shaped member having a first leg 20 connected to a second leg 22 by a connecting portion 24. Each of the legs 20 and 22 carries a device for firmly attaching the yoke 16 to one of a pair of articulated bones such as the tibia. In the embodiment shown in the figures, that attachment device takes the form of spikes 26 and 28 carried by the first and second legs 20 and 22, respectively. In the alternative, each spike 26 and 28 may be replaced by a bore suitable for allowing the yoke 16 to be attached to the tibia through the use of Kirshner wires. The connecting portion 24 of the yoke 16 has a pair of bores 30 and 32 extending therethrough at an angle. The bores 30 and 32 can each receive a Kirshner wire such that when the footplate 10 is attached to the tibia, two crossed Kirschner wires can be used to firmly affix the footplate 10.

Each of the legs 20 and 22 has a first aperture 44 and a second aperture 48 extending therethrough. The function of those apertures is discussed below in conjunction with the yoke plate 18.

The yoke plate 18 carries a pair of blunt pins 34 and 36. The blunt pins facilitate connection of the yoke plate 18 with the impactor 12 or tensiometer assembly 14 as explained more fully hereinbelow. The yoke plate 18 includes a pair of hinge members 38 and 40 extending in a direction opposite from the direction in which the blunt pins 34 and 36 extend. Each of the hinge members 38 and 40 has a first aperture 42 extending therethrough. The first aperture 42 of the hinge member 38 may be aligned with the first aperture 44 of the first leg 20 while the first aperture 42 of the hinge member 40 may be aligned with the first aperture 44 of the second leg 22. After alignment, hinge pins (not shown) may be inserted through the aforementioned aligned apertures such that yoke plate 18 is rotatably carried by the yoke 16.

Figure 12:
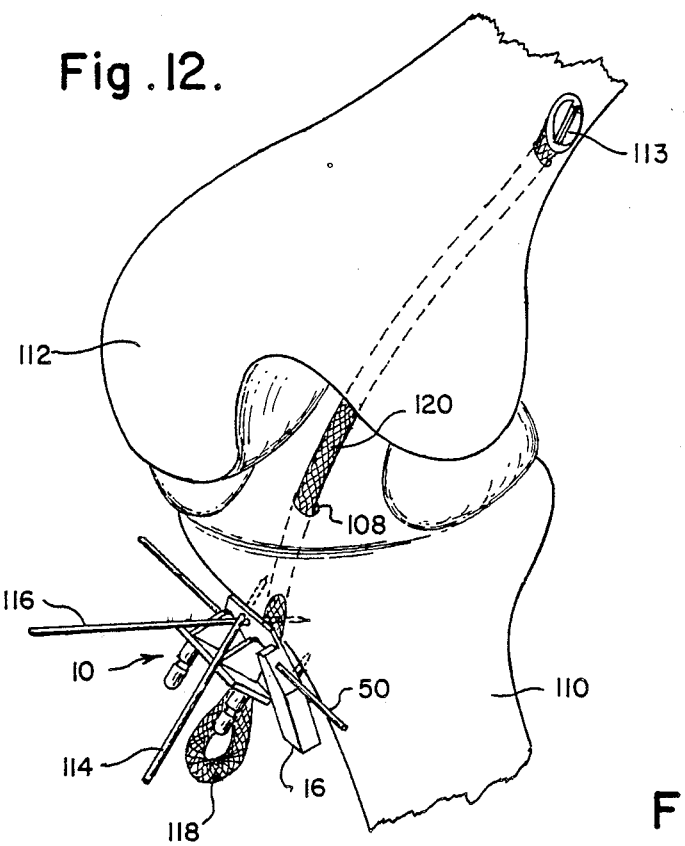
FIG. 12 illustrates the footplate firmly attached to the tibia.

Each of the hinge members 38 and 40 carries a second aperture 46. Upon rotation of the yoke plate 16 in a counterclockwise direction as shown by the arrow in FIG. 1, the second apertures 46 of the hinge members 38 and 40 can be brought into alignment with the second apertures 48 of the first and second legs 20 and 22, respectively. Upon alignment of the aforementioned apertures, a locking wire 50 seen in FIG. 12 may be inserted through the aligned apertures to maintain the footplate in the locked position. Thus, the footplate 10 may assume an unlocked position as shown in FIG. 1, or a locked position as shown in FIG. 12.

Figure 6:
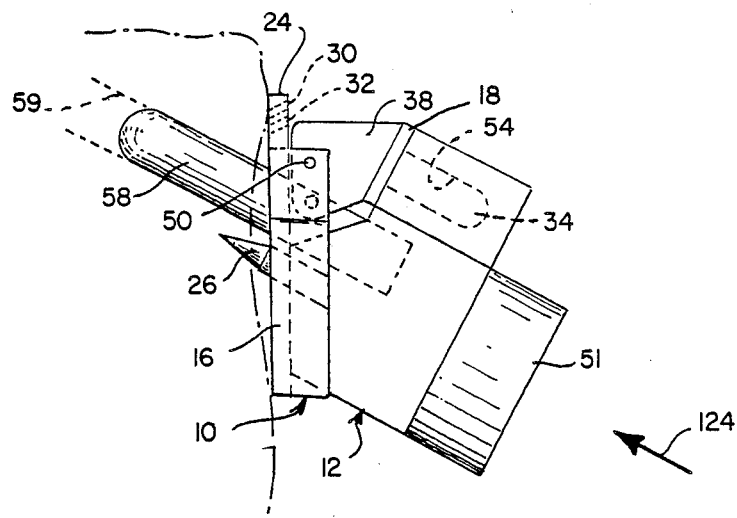
FIG. 6 is a side view of the impactor connected to the footplate with the footplate in a locked position and a guide pin of the impactor engaging a tibial tunnel.

The impactor 12 of the present invention is illustrated in perspective in FIGS. 4 and 5. The impactor 12 has a rear portion 51 which is capable of absorbing a substantial amount of force as would be generated when the impactor 12 is struck, for example, with a hammer. A front portion 52 of the impactor 12 carries a first aperture 54 adapted for receiving the first blunt pin 34 of the yoke plate 18 and a second aperture 56 adapted for receiving the second blunt pin 36 of the yoke plate 18. In that manner, the impactor 12 may be carried by the footplate 10 as shown in FIG. 6. As can be seen from the figures, the front portion 52 of the impactor 12 has a shape which is complimentary to the shape of the footplate such that force absorbed by the rear portion 51 may be efficiently transmitted to the footplate 10.

The front portion 52 of the impactor 12 carries an alignment pin 58. When the impactor 12 is carried by the footplate 10 as shown in FIG. 6, the alignment pin 58 extends through the open portion of the U-shaped yoke 16. The alignment pin 58 is carried by the front portion 52 in such a manner that when the footplate is in the locked position as shown in FIG. 6, the alignment pin 58 is substantially parallel to the first and second spikes 26 and 28. In the event the spikes 26 and 28 are eliminated in favor of a pair of Kirshner wires, the pin 58 need only be in line with a bony tunnel 59 as illustrated in FIG. 6. Various impactors with alignment pins 58 extending at angles which are, for example, in ten degree increments may be provided so that the surgeon can select the proper impactor. The function of the alignment pin is discussed hereinbelow.

Figure 11:
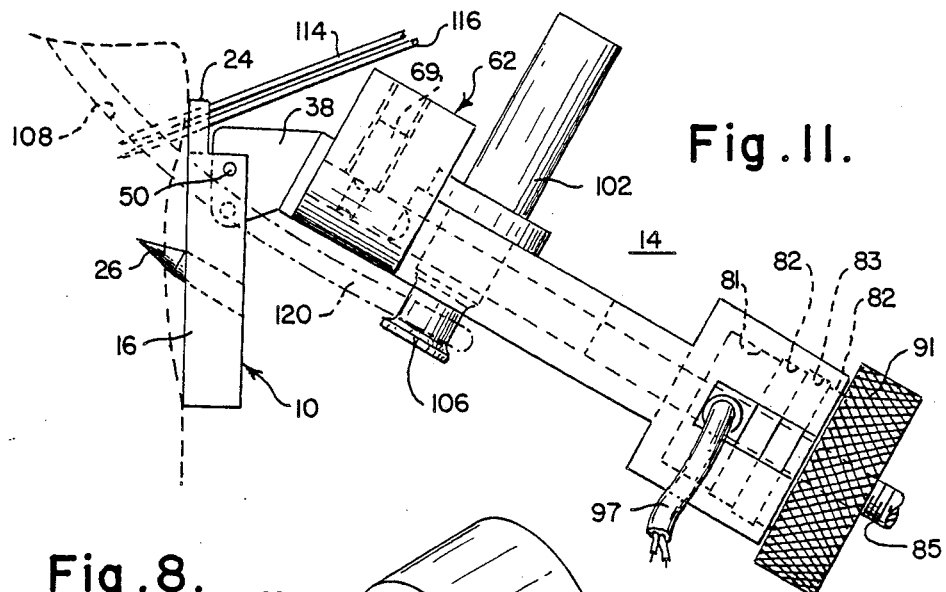
FIG. 11 illustrates the full tensiometer assembly connected to the footplate with the footplate in the locked position and firmly attached to the tibia.
Figure 8:
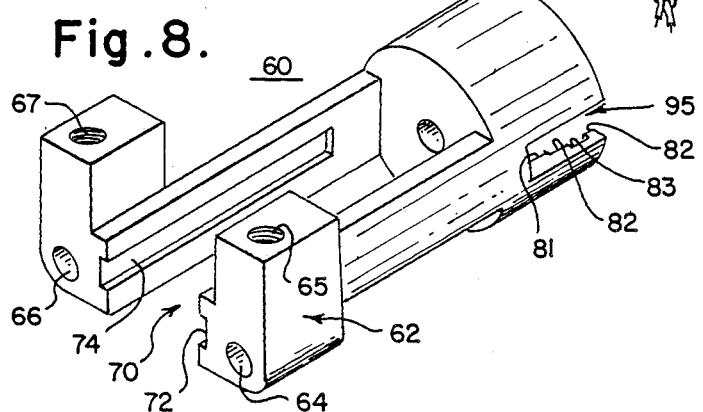
FIG. 8 is a perspective view of a main housing of the tensiometer assembly.

The third part of the present invention is the tensiometer assembly 14 which is shown in FIG. 7. The tensiometer assembly 14 is comprised of a main housing 60, a perspective view of which is illustrated in FIG. 8. The main housing 60 has a forward clamping portion 62. The forward clamping portion has a first horizontal aperture 64 intersected by a first vertical aperture 65 and a second horizontal aperture 66 intersected by a second vertical aperture 67. The horizontal apertures 64 and 66 of the main housing 60 are adapted to receive the blunt pins 34 and 36, respectively, of the yoke plate 18. The vertical apertures 65 and 67 are adapted to receive set screws 69 which set screws hold bearings (not shown) to enable a ball detent junction with the blunt pins 34 and 36 positioned in the horizontal apertures 64 and 66, respectively. In that manner, the tensiometer 14 can be securely fastened to the footplate 10 as shown in FIG. 11.

The main housing 60 has a central open area 70 which is bounded by slots 72 and 74. The slots 72 and 74 are adapted to receive wings 76 of a sled 78 seen best in FIG. 9. When the wings 76 of the sled 78 are positioned in slots 72 and 74, the movement of the sled 78 is restricted to horizontal translation as viewed in FIG. 7.

Referring to FIGS. 7 and 9, the rear portion of the main housing 10 has an aperture therethrough which has four different diameters as indicated by reference numbers 80 through 83. At reference numeral 80, the aperture has a diameter sufficient to allow a threaded bolt 85 to pass therethrough. The threaded bolt 85 is fixedly carried by the sled 78 as shown in FIG. 9A, and extends beyond the main housing 60 as shown in FIG. 7. The diameter of the aperture at 81 is sufficient to enable a transducer 87 to fit therein. The transducer 87 may be a load cell or load washer such as those available from Kistler. The load cell fits within the aperture at diameter 81 in such a manner that a small portion of the load cell extends into the aperture in the area of diameter 82.

The aperture at diameter 82 is sufficient to receive a forwardly extending portion 89 of a threaded nut 91. The threaded nut 91 is then threaded upon the threaded bolt 85 until the extending portion 89 contacts the transducer 87. In such a configuration, rotation of the threaded nut 91 in one direction urges the sled 78 toward the threaded nut 91 while rotation of the threaded nut 91 in the opposite direction urges the sled 78 away from the threaded nut 91. Additionally, movement of the transducer 87 is restrained in one direction by virtue of the main housing 60 and is restrained from movement in the other direction by the extended portion 89 of the threaded nut 91.

The diameter of the aperture at 83 is slightly larger than the diameter of the aperture at 82 so as to form a groove. Spring loaded balls 93 carried by the extended portion 89 ride in the groove formed by the larger diameter of the aperture at 83. The spring loaded balls 93 establish a minimal amount of drag on the threaded nut 91 such that the threaded nut 91 does not inadvertently move. They also prevent the threaded nut from falling away from the main housing 60 in the event that the threaded bolt is removed therefrom.

The main housing 60 also carries a slot 95, best seen in FIG. 8, through which transducer wires 97 may extend when the transducer is positioned within the main housing 60 as illustrated in FIG. 7.

Returning to FIG. 9, sled 78 has an aperture 99 extending therethrough. The aperture 99 is adapted to receive a drill sleeve 102. The drill sleeve 102 may be held in place by spring loaded balls 105, or other suitable means of fixation, positioned within threaded bores 107. When the drill sleeve is held in place in aperture 99, the drill sleeve 102 is perpendicular to the sled 78. The drill sleeve 102 has a central bore 104 adapted for receiving a drill bit or the like. The drill sleeve 102 has a first end 106 adapted for receiving a loop formed in either a trial ligament or the ligament graft. Alternatively, the sled can be constructed to mate with a variety of different tools. The complete tensiometer assembly 14 is shown connected to the footplate 10, with the footplate 10 in the locked position, in FIG. 11.

Method of Use

A method of using the apparatus of the present invention will now be described in conjunction with FIGS. 6 and 11 through 14 wherein the cruciate ligament of the knee is being replaced. However, the apparatus and method of the present invention can be used to measure the variation in tension of a ligament graft extending through a bore between first and second fixation sites positioned on first and second articulated bones, respectively.

Referring to FIG. 12, as is known, the cruciate ligament is connected at one end to a femur 112 and at the other end to a tibia 110. Replacement of the cruciate ligament requires at least one tunnel 108 in the tibia 110. There are alternatives for the path of the replacement ligament at the femoral side of the joint. When the tibial tunnel 108 has been drilled and the femoral path has been decided, including a fixation site 113 on the femur 112, the impactor 12 is connected to the footplate 10 with the footplate in the locked position as is shown in FIG. 6. The alignment pin 58 of the impactor 12 fits into the bony tunnel 59 which in this example is the tibial tunnel 108. With the alignment pin thus positioned, the first and second spikes 26 and 28 may be driven into the tibia 110 by supplying sufficient force to the rear portion 51 of the impactor 12, such as with a hammer, in the direction indicated by arrow 124. As the spikes 26 and 28 are driven into the tibia 110, the alignment pin 58 advances in the tibial tunnel 108 thus insuring that the footplate 10 is precisely positioned relative to the exit of the tunnel 108 from the tibial surface.

If an alternative embodiment is used which employs the Kirshner wires instead of the spikes, then an impactor having a guide pin 58 having the desired angle is used. After the guide pin is fully inserted into the tibial tunnel 108 and the footplate properly positioned, the two Kirschner wires used in place of the spikes are inserted.

Referring back to FIG. 12, before the impactor 12 is removed, a pair of crossed Kirschner wires 114 and 116 are inserted into the tibia 110 through the bores 30 and 32 of the footplate 10. Kirschner wires 114 and 116 lock the footplate 10 onto the tibia 110. After that is completed, the impactor 12 can be removed and replaced by the tensiometer 14 as shown in FIG. 11.

With the tensiometer 14 so positioned, a loop 118 (seen best in FIG. 12) formed in a ligament graft 120 is positioned around the first end 106 of the sleeve 102. It should be apparent to those of ordinary skill in the art that the procedure being described herein is first performed with a trial device (not shown) having a much smaller diameter than the diameter of the ligament 120 seen in FIGS. 11 through 14. When an acceptable set of mechanics has been determined with the trial device, the trial device is removed and the tibial tunnel 108 enlarged to accommodate the replacement ligament 120. Thereafter, the regimen of tests used to establish the acceptable set of mechanics can be performed again on the ligament 120 to confirm the fixation sites.

Figure 14:
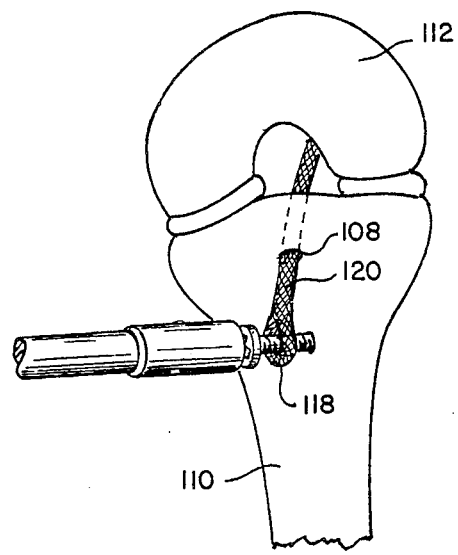
FIG. 14 illustrates a ligament graft being attached to the tibia.

Returning to FIG. 11, with the tensiometer 14 thus positioned, the threaded nut 91 is rotated to provide a desired degree of tension on the ligament 120 as indicated by the output of the transducer 87. The output of the transducer 87 may be a continuous readout of the tension sensed by the transducer 87 and/or a strip chart recorder. After establishing the initial degree of tension, the joint may be moved through a complete range of motion or any desired regimen of tests can be performed while the forces developed can be viewed and recorded. When the surgeon is satisfied that the fixation sites are correct, the locking wire 50 is removed and the yoke plate 18 rotated so that the footplate 10 is in the unlocked position as shown in FIG. 13. With the footplate 10 in the unlocked position, the drill sleeve 102 is positioned perpendicularly with respect to the surface of the tibia 110. With such an orientation, a drill 122 or the like may be inserted in the bore 104 of the drill sleeve 102 to drill a pilot or guide hole for a screw. The drill sleeve 102 protects the ligament 120 while the pilot hole is being drilled. Thereafter, the instrument of the present invention may be removed and the replacement ligament 120 attached to the fixation site as determined by the position of the pilot hole. That is shown in FIG. 14.

At different times during the surgery, the tensiometer 14 can be removed to facilitate the surgeon's work without jeopardizing the accuracy of the position of the replacement ligament 120 because the footplate 10 is securely fastened to the tibia 110. The sled 78 of the tensiometer 14 can accommodate a variety of tools (not shown) which can be attached to the replacement ligament 120. Such flexibility is desireable so that the present invention can be used for implanting a broad range of replacement devices. Additionally, the sled 78 can be fitted with a small tool, like a nerve hook (not shown), to be used arthroscopically to test the integrity of the ligament by allowing the surgeon to measure the force that he is putting on the ligament in the joint to deform it. In that use, the footplate 10 is not necessary.

In addition to varying sled designs, there is no reason to restrict the instrument of the present invention to a measurement of compression only. A transducer capable of measuring both tension and compression may be provided or a second transducer positioned in a mirror image fashion to the transducer 87 may be provided.

While the present invention has been described in conjunction with a preferred embodiment thereof, many modifications and variations will be readily apparent to those of ordinary skill in the art. For example, two instruments constructed according to the teachings of the present invention may be used simultaneously to replace both the anterior and posterior cruciate ligaments. Another modification could include eliminating the guide pin 58 from the impactor and providing the impactor with a slot to receive the end of the pilot drill extending through the tibial tunnel. This disclosure and the following claims are intended to cover all such modifications and variations.

What is claimed is:

1. An instrument for determining the variation in tension of a ligament graft extending between first and second fixation sites positioned on first and second articulated bones, respectively, comprising:
   a yoke, said yoke having means for securing said yoke to one of the first and second bones;
   a yoke plate rotatably mounted to said yoke;
   main housing means, said housing means for connection to said yoke plate;
   sled means slidably connected to said main housing, said sled means for connection to the ligament graft and thereby defining one of the first and second fixation sites, respectively;
   means for adjusting the position of said sled means relative to said housing means so as to place a desired degree of tension on the ligament graft; and
   transducer means associated with said means for adjusting for determining changes in tension from said desired degree as the first and second bones are moved relative to one another.

2. The instrument of claim 1 wherein said yoke is U-shaped and wherein said means for securing includes spikes extending at an angle from the legs of said U-shaped yoke.

3. The instrument of claim 2 additionally comprising an impactor having first surface means for connection to said yoke plate, said impactor having alignment pin means for insertion into a pilot hole drilled through said one of the bones and extending from said first surface means at an angle such that said alignment pin means is substantially parallel to said spikes, said impactor having a substantially smooth second surface opposite said first surface means.

4. The instrument of claim 1 wherein said means for adjusting the position of said sled means includes a threaded bolt extending longitudinally from said sled means and a threaded nut, said main housing means also for preventing lateral movement of said threaded nut, said nut receiving said threaded bolt such that rotation of said nut in one direction urges said sled means toward said threaded nut and rotation in the other direction urges said sled means away from said threaded nut.

5. The instrument of claim 4 wherein said transducer means is interposed between said threaded nut and said main housing so as to be in line with the ligament graft.

6. The instrument of claim 5 wherein said transducer means includes a load cell.

7. The instrument of claim 1 wherein said yoke plate can be rotated between a first position wherein said main housing means is angled away from said yoke and a second position wherein said main housing means is parallel to said yoke.

8. The instrument of claim 7 additionally comprising a drill sleeve connected to said sled means so as to be perpendicular to said yoke when said yoke plate is in said second position.

9. An instrument for measuring the variation in tension of a ligament graft extending from a first fixation site on a patient's femur through a tibial tunnel toward a second fixation site on the patient's tibia, comprising;
 a yoke, said yoke having means for securing said yoke to the tibia;
 a main housing;
 yoke plate means for connection to said main housing, said yoke plate means also for rotatable connection to said yoke such that said main housing is in line with the tibial bore when said yoke plate means is in a first position and is parallel to the tibia when said yoke plate means is in a second position;
 a sled slidably connected to said main housing;
 a drill sleeve connected to said sled and having portion means thereof for receiving a loop formed in the end of the ligament graft thereby defining said second fixation site;
 means for adjusting the position of said sled relative to said housing so as to place a desired degree of tension on the ligament graft; and
 transducer means associated with said means for adjusting for measuring changes in tension from said desired degree as the tibia is moved relative to the femur.

10. A method of measuring the variation in tension of a ligament graft extending through a bore between a first and second fixation sites positioned on first and second articulated bones, respectively, comprising the steps of:
 positioning an alignment device on a footplate;
 using the alignment device to position the footplate relative to the bore;
 securing said footplate to one of the first and second bones;
 removing said alignment device and connecting a housing having a sled, means for adjusting the position of said sled relative to said housing, and a transducer to said footplate;
 connecting the ligament graft to said sled and thereby forming one of the first and second fixation sites, respectively;
 adjusting the tension on the ligament graft with said adjustment means to place a desired degree of tension on the ligament graft; and
 measuring changes in tension from said desired degree with said transducer as the first and second bones are moved relative to one another.

11. The method of claim 10 wherein the footplate has spikes extending therefrom, and wherein the step of securing includes the step of driving said spikes into said one of the first and second bones.

12. The method of claim 10 wherein the footplate includes bores, and wherein the step of securing includes the step of inserting two crossed Kirschner wires through the bores in said footplate into said one of the first and second bones.

13. The method of claim 10 wherein the sled includes a drill guide sleeve, and wherein the step of connecting the ligament graft includes inserting drill guide sleeve connected to said sled through a loop in the end of the ligament graft.

14. The method of claim 13 additionally comprising the step of rotating said housing with respect to said footplate so that said drill guide sleeve is perpendicular to said one of the first and second bones.

15. The method of claim 14 including the step of holding the ligament tension constant during rotation of the housing.

* * * * *

UNITED STATES PATENT AND TRADEMARK OFFICE
CERTIFICATE OF CORRECTION

PATENT NO. : 4,969,895

DATED : November 13, 1990

INVENTOR(S) : William McLeod, Paul Wisnewski, David Evans and Mark Gosney

It is certified that error appears in the above-identified patent and that said Letters Patent is hereby corrected as shown below:

Col. 7, line 13, insert --The-- after "10".

Col. 10, line 32, insert --the-- after "inserting" and before "drill".

Signed and Sealed this

Eleventh Day of August, 1992

Attest:

DOUGLAS B. COMER

*Attesting Officer*     *Acting Commissioner of Patents and Trademarks*